(12) United States Patent
Freeling et al.

(10) Patent No.: US 7,408,637 B2
(45) Date of Patent: Aug. 5, 2008

(54) ENTANGLED PHOTON SPECTROSCOPY FOR STAND-OFF DETECTION AND CHARACTERIZATION

(75) Inventors: Richard Freeling, Brighton, MI (US); Kenneth Augustyn, Plymouth, MI (US)

(73) Assignee: General Dynamics Advanced Information Systems, Inc., Arlington, VA (US)

( * ) Notice: Subject to any disclaimer, the term of this patent is extended or adjusted under 35 U.S.C. 154(b) by 158 days.

(21) Appl. No.: 11/088,206

(22) Filed: Mar. 24, 2005

(65) Prior Publication Data

US 2005/0243324 A1    Nov. 3, 2005

Related U.S. Application Data

(60) Provisional application No. 60/555,675, filed on Mar. 24, 2004.

(51) Int. Cl.
*G01J 3/00*    (2006.01)

(52) U.S. Cl. ........................ 356/317; 356/300

(58) Field of Classification Search .............. 356/317, 356/318, 417
See application file for complete search history.

(56) References Cited

U.S. PATENT DOCUMENTS

| | | | |
|---|---|---|---|
| 4,225,938 A | 9/1980 | Turpin |
| 4,286,328 A | 8/1981 | Bocker |
| 4,468,093 A | 8/1984 | Brown |
| 4,633,427 A | 12/1986 | Bocker |
| 5,339,182 A | 8/1994 | Kimble et al. |
| 5,420,905 A | 5/1995 | Bertozzi |
| 5,796,477 A | 8/1998 | Teich et al. |
| 5,917,322 A | 6/1999 | Gershenfeld et al. |
| 6,057,541 A | 5/2000 | Steenblik |
| 6,252,665 B1 | 6/2001 | Williams et al. |
| 6,289,104 B1 | 9/2001 | Patterson et al. |
| 6,314,189 B1 | 11/2001 | Motoyoshi et al. |
| 6,424,665 B1 | 7/2002 | Kwiat et al. |
| 6,430,345 B1 | 8/2002 | Dultz et al. |
| 6,444,999 B1 | 9/2002 | Tomita |
| 6,473,719 B1 | 10/2002 | Steenblik |
| 6,480,283 B1 | 11/2002 | Williams et al. |

(Continued)

FOREIGN PATENT DOCUMENTS

EP    1091240    4/2001

(Continued)

OTHER PUBLICATIONS

Strekalov et al., Two-photon processes in faint biphoton fields, pp. 1-18, downloaded Mar. 9, 2005, http://arxiv.org.

(Continued)

*Primary Examiner*—F. L Evans
(74) *Attorney, Agent, or Firm*—Hunton & Williams LLP

(57) ABSTRACT

A system for and method of detecting and characterizing materials using entangled photons is presented. The material may be at a great distances from the detector and may be biological material, complex organic compounds, or inorganic chemicals. The disclosed system and method provide advantages over traditional techniques in that they are largely impervious to atmospheric reduction of probing radiation and in that less probing radiation is required. The reduced probe energy requirement allows for detecting and characterizing sensitive material with significantly reduced material bleaching compared with traditional techniques.

33 Claims, 10 Drawing Sheets

U.S. PATENT DOCUMENTS

| | | | |
|---|---|---|---|
| 6,522,749 | B2 | 2/2003 | Wang |
| 6,646,727 | B2 | 11/2003 | Saleh et al. |
| 6,678,054 | B1 | 1/2004 | Dress et al. |
| 2002/0018290 | A1 | 2/2002 | Birk et al. |
| 2002/0020819 | A1 | 2/2002 | Wolleschensky et al. |
| 2002/0036775 | A1 | 3/2002 | Wolleschensky et al. |
| 2002/0093632 | A1 | 7/2002 | Teich et al. |
| 2002/0109840 | A1 | 8/2002 | Wolleschensky et al. |
| 2002/0140941 | A1 | 10/2002 | Pedigo |
| 2003/0002670 | A1 | 1/2003 | Wang |
| 2003/0086138 | A1 | 5/2003 | Pittman et al. |
| 2004/0036877 | A1 | 2/2004 | Sergienko et al. |
| 2004/0208638 | A1 | 10/2004 | Jansen |
| 2005/0206904 | A1* | 9/2005 | Zaugg ........................ 356/451 |

FOREIGN PATENT DOCUMENTS

| | | | |
|---|---|---|---|
| WO | WO 02/45468 | A2 | 6/2002 |
| WO | WO 03/019282 | A2 | 3/2003 |
| WO | WO 03/019283 | A2 | 3/2003 |
| WO | WO 03/019284 | A2 | 3/2003 |

OTHER PUBLICATIONS

Enzer et al., Entangled-photon six-state quantum cryptography, New Journal of Physics 4 (2002) 45.1-45.8.

Gatti et al., Multi-photon, multi-mode polarization entanglement in parametric down-conversion, pp. 1-22 (download date unknown), http://arxiv.org.

Bouwmeester et al., Experimental quantum teleportation, Nature, vol. 390, Dec. 11, 1997, pp. 575-579.

Sciarrino et al., Delayed-choice entanglement swapping with vacuum-one-photon quantum states, Physical Review A, 66, 024309 (2002).

Sergienko et al., Quantum cryptography with femtosecond parametric down conversion, Quantum Imaging Laboratory, pp. 1-8, undated.

Altepeter et al., Ancilla-assisted quantum process tomography, Physical Review Letters, vol. 90, No. 19, May 16, 2003, 193601-to 193601-4.

Oneil, Quantum information studies, Department of Experimental Physics, {http://www.may.ie/academic/physics/quantum.shtml}, printed Feb. 25, 2004, 2 pages.

Giacomini et al., Active teleportation of a quantum bit, Physical Review A, 66, 030302(R) (2000).

Jost et al., Spatial correlations of spontaneously down-converted photon pairs detected with a single-photon-sensitive CCD camera, Optics Express 81, Jul. 20, 1998, vol. 3, No. 2.

Caetano et al., Quantum image control through polarization entanglement in parametric down-conversion, Physical Review A 68, 023805 (2003).

Barbosa, Twin photons entangled in polarization and angular momentum, Eur. Phys. J. D22, 433-440 (2003).

Ribeiro et al., Image and coherence transfer in the stimulated down-conversion process, Physical Review A, vol. 60, No. 6, Dec. 1999, 5074-5078.

Monken et al., Transfer of angular spectrum and image formation in spontaneous parametric down-conversion, Physical Review A, vol. 57, No. 4, Apr. 1998, 3123-3126.

Ribeiro et al., Observation of image transfer and phase conjugation in stimulated down-conversion, Physical Review Letters, vol. 87, No. 13, Sep. 24, 2001, 133602-1 to 133602-4.

Fonseca et al., Quantum interference by a nonlocal double slit, Physical Review A, vol. 60, No. 2, Aug. 1999, 1530-1533.

Atature et al., Entanglement in cascaded-crsytal parametric down-conversion, Physical Review Letters, vol. 86, No. 18, Apr. 30, 2001, 4013-4016.

White et al., Nonmaximally entangled states: production, characterization, and utilization, Physical Review Letters, vol. 83, No. 16, Oct. 18, 1999, 3103-3107.

Kwiat et al., Ultrabright source of polarization-entangled photons, Physical Review A, vol. 60, No. 2, Aug. 1999, 773-776.

Kwiat et al., Experimental entanglement distillation and "hidden" non-locality, Letter to Nature, 1014-1017, 2001.

Grover, Quantum computers can search arbitrarily large databases by a single query, Physical Review Letters vol. 79, No. 23, Dec. 8, 1997, 4709-4712.

Berthiaume et al., The quantum challenge to structural complexity theory, 132-137, undated.

Ekert et al., Quantum computation and Shor's factoring algorithm, Reviews of Modern Physics, vol. 68, No. 3, Jul. 1996, 733-753.

Blum, Density matrix theory and applications, 1-217, 1981.

Zhang et al., Experimental and theoretical aspects of quantum teleportation, Center for Engineering Science Advanced Research, 9 pages, undated.

Abouraddy et al., Degree of entanglement for two qubits, Physical Review A, vol. 64, 050101-1 to 050101-4, Oct. 8, 2001.

Semat et al., Introduction to Atomic and Nuclear Physics, Fifth Edition, Chp. 7, Elements of quantum mechanics, 186-215, undated.

Ekert, Quantum cryptography based on Bell's theorem, Physical Review Letters, vol. 67, No. 6, Aug. 5, 1991, 661-663.

Schenker, A quantum leap in codes for secure transmissions, International Herald Tribune, printed Apr. 12, 2004, {http://www.iht.com/articles/126822.html}, 3 pages.

Johnson, Magiq employs quantum technology for secure encryption, Advanced Technology, printed Apr. 12, 2004 {http://www.eetimies.com/at/news/OEG20021105S0019}, 3 pages.

McCulagh, Start-up makes quantum leap into cryptography, C/NET News.com, printed Apr. 12, 2004, {http://news.com.com/2100-1029-5103373.html}, 3 pages.

Scully et al., Two-photon scheme for detecting the Bell basis using atomic coherence, Physical Review Letters, vol. 83, No. 21, Nov. 22, 1999, 4433-4436.

Braunstein et al., Dense coding for continuous variables, Physical Review A, vol. 61, 042302-1 to 04302-4, Mar. 3, 2000.

Santos et al., Measurement of the degree of polarization entanglement through position interference, Physical Review A, vol. 64, 023804-1 to 023804-6, Jul. 9, 2001.

Saleh et al., Entangled-photon virtual-state spectroscopy, Physical Review Letters, vol. 80, No. 16, Apr. 20, 1998, 3483-3486.

Oberparleiter et al., Optics Communications, 183 (2000) 133-137.

Georgiades et al., Nonclassical excitation for atoms in a squeezed vacuum, Physical Review Letters, vol. 75, No. 19, Nov. 6, 1995, 3426-3429.

Joobeur et al., Spatiotemporal coherence properties of entangled light beams generated by parametric down-conversion, Physical Review A, vol. 50, No. 4, Oct. 1994, 3349-3361.

Nasr et al., Biphoton focusing for two-photon excitation, Physical Review A, vol. 65, 023816-1 to 023816-6, Jan. 17, 2002.

Abouraddy et al., Role of entanglement in two-photon imaging, Physical Review Letters, vol. 87, No. 12, Sep. 17, 2001, 123602-1 to 123602-4.

Boeuf et al., Calculating characteristics of non-collinear phase-matching in uniaxial biaxial crystals, Optical Technology Division, pp. 1-24, draft Aug. 27, 1999.

Abouraddy et al., Double-slit interference of biphotons generated in spontaneous parametric downconversion from a thick crystal, Journal of Optics B: Quantum and Semiclassical Optics 3, 2001, S50-S54.

Kwiat et al., Experimental verification of decoherence-free subspaces, Science, vol. 290, Oct. 20, 2000, 498-500.

Naik et al., Entangled state quantum cryptography: eavesdropping on the Eckert protocol, Physical Review Letters, vol. 84, No. 20, May 15, 2000, 4733-4736.

Yabushita et al., Spectroscopy by frequency entangled photon pairs, pp. 1-11(download date unknown), http://arxiv.org.

Perina et al., Multiphoton absorption cross section and virtual-state spectroscopy for the entangled $n$-photon state, Physical Review A, vol. 57, No. 5, May 1998, pp. 3972-3986.

Fei et al., Entangled-induced two-photon transparency, Physical Review Letters, vol. 78, No. 9, Mar. 3, 1997, pp. 1679-1682.

Yabushita et al., Spectroscopy by frequency entangled photon pairs, Physical Review A 69. 013806-1-013806-4 (2004).

Kurtsiefer et al., High-efficiency entangled photon pair collection in type-II parametric fluorescence, Physical Review A, vol. 64, 023802-1 to 0283802-4, Jul. 2, 2001.

Jost et al., Spatial correlations of spontaneously down-converted photon pairs detected with a single-photon-sensitive CCD camera, Optics Express, Jul. 20, 1998, vol. 3, No. 2, pp. 81-88.

Almeida et al., Transmission of quantum images through long distances, pp. 1-4, (download date unknown), http://arxiv.org.

Caetano et al., Quantum Physics, Abstract, Image formation by manipulation of the entangled angular spectrum, pp. 1-5, (download date unknown), http://arxiv.org.

Zavatta, Premio Italgas/Italgas Prize Energy and Environment 16$^{th}$ Edition, Summary of the Thesis "Debut in the World of Research", undated.

Rubin et al., Theory of two-photon entanglement in type-II optical parametric down-conversion, Physical Review A, vol. 50, No. 6, Dec. 1994, pp. 5122-5133.

Rarity et al., Experimental demonstration of single photon rangefinding using parametric downconversion, Applied Optics, vol. 29, No. 19, Jul. 1, 1990, pp. 2939-2943.

Waks et al., Security of quantum key distribution with entangled photons against individual attacks, Physical Review A, vol. 65, 052310-1 to 052310-16, 2002.

Ribeiro et al., Observation of image transfer and phase conjugation in stimulated down-conversion, pp. 1-6, (download date unknown), http://arxiv.org.

Caetano et al., Image-polarization entanglement in parametric down-conversion, 4 pages, undated.

Ribeiro et al., Image and coherence transfer in the stimulated down-conversion process, pp. 1-5, (download date unknown), http://arxiv.org, Dec. 1999.

Caetano et al., Quantum distillation of position entanglement with the polarization degrees of freedom, ScienceDirect, Optics Communications, Mar. 3, 2004, (www.sciencedirect.com/science).

Law et al., Analysis and Interpretation of High Transverse Entanglement in Optical Parametric Down Conversion, Physical Review Letters, vol. 92, No. 12, Mar. 26, 2004.

O'Sullivan-Hale et al., Pixel Entanglement: Experimental Realization of Optically Entangled $d=3$ and $d=6$ Qudits, Physical Review Letters, vol. 92, No. 12, Jun. 10, 2005.

\* cited by examiner

ENTANGLED PHOTON SPECTROSCOPY FOR STAND-OFF DETECTION AND CHARACTERIZATION

CROSS-REFERENCE TO RELATED APPLICATIONS

The present application claims priority to U.S. Provisional Patent Application No. 60/555,675, to Freeling et at, entitled "Entangled-Photon Spectroscopy for Stand-Off Detection and Characterization," filed on Mar. 24, 2004, the disclosure of which is expressly incorporated by reference herein in its entirety. The present application further incorporates by reference in its entirety U.S. Utility Patent Application Ser. No. 10/850,394, to Kastella et at, entitled "System and Method of Detecting Entangled Photons," filed on May 21, 2004.

GOVERNMENT INTERESTS

To the extent that this invention was made with government support under contract number-F33615-99-D-1501, delivery order 0009, awarded by the U.S. Air Force, the government has certain rights in this invention.

BACKGROUND OF THE INVENTION

1. Field of the Invention

The invention relates to ascertaining properties of a material using entangled photons. In particular, the invention relates to directing entangled photons to a material, possibly located at a distance from the source of entangled photons, in order to ascertain properties of the material by detecting evidence of entangled photon absorption by the material.

2. Discussion of Background Information

Photons are quanta of electromagnetic energy. Multiple photons may be entangled or not entangled. Photons that are not entangled together (i.e., random photons) exist as independent entities. In contrast, entangled photons have a connection between their respective properties.

Two photons entangled together are referred to as an entangled-photon pair (also, "biphotons"). Traditionally, photons comprising an entangled-photon pair are called "signal" and "idler" photons. Measuring properties of one photon of an entangled-photon pair determines results of measurements of corresponding properties of the other photon, even if the two entangled photons are separated by a distance. As understood by those of ordinary skill in the art and by way of non-limiting example, the quantum mechanical state of an entangled-photon pair cannot be factored into a product of two individual quantum states.

In general, more than two photons may be entangled together. More than two photons entangled together are referred to as "multiply-entangled" photons. Measuring properties of one or more photons in a set of multiply-entangled photons restricts properties of the rest of the photons in the set by constraining measurement outcomes. As understood by those of ordinary skill in the art and by way of non-limiting example, the quantum mechanical state of a set of n>2 multiply-entangled photons cannot be factored into a product of n separate states. The term "entangled photons" refers to both biphotons and multiply-entangled photons.

General techniques for ascertaining spectroscopic properties of materials are known. Such techniques typically rely on directing non-entangled (random) photons at a material, which absorbs the photons and emits fluorescence. In general, these techniques rely on varying the frequency of the non-entangled photons. By comparing incident photon energy with the energy of resulting fluorophotons, the absorbing material may be crudely characterized.

SUMMARY OF THE INVENTION

According to an embodiment of the present invention, a system for and method of determining spectroscopic properties of a material are presented. The method comprises producing entangled photons having at least one known entangled photon parameter and directing the entangled photons to a material. Fluorescence resulting from entangled photon absorption by the material is observed, and spectroscopic properties of the material are deduced from the at least one known entangled photon parameter and the fluorescence observations. The spectroscopic properties of the material are deduced from a relationship between absorption characteristics determined by the fluorescence observations and the known entangled photon parameters.

Various optional and preferable features and advantages of embodiments of the present invention include the following. Materials that may be detected and characterized include organic materials, biological materials, and inorganic materials. The probing radiation may be selected to be easily transmitted by the atmosphere. A material may be detected and characterized at a great distance from the invention embodiment. Low-energy probing radiation may be used, which results in reduced material bleaching when compared to traditional techniques.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of non-limiting examples of certain embodiments of the present invention, in which like numerals represent like elements throughout the several views of the drawings, and wherein.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, the description taken with the drawings provides a fundamental understanding of the present invention, making apparent to those skilled in the art how the several forms of the present invention may be embodied in practice.

Figure 1:
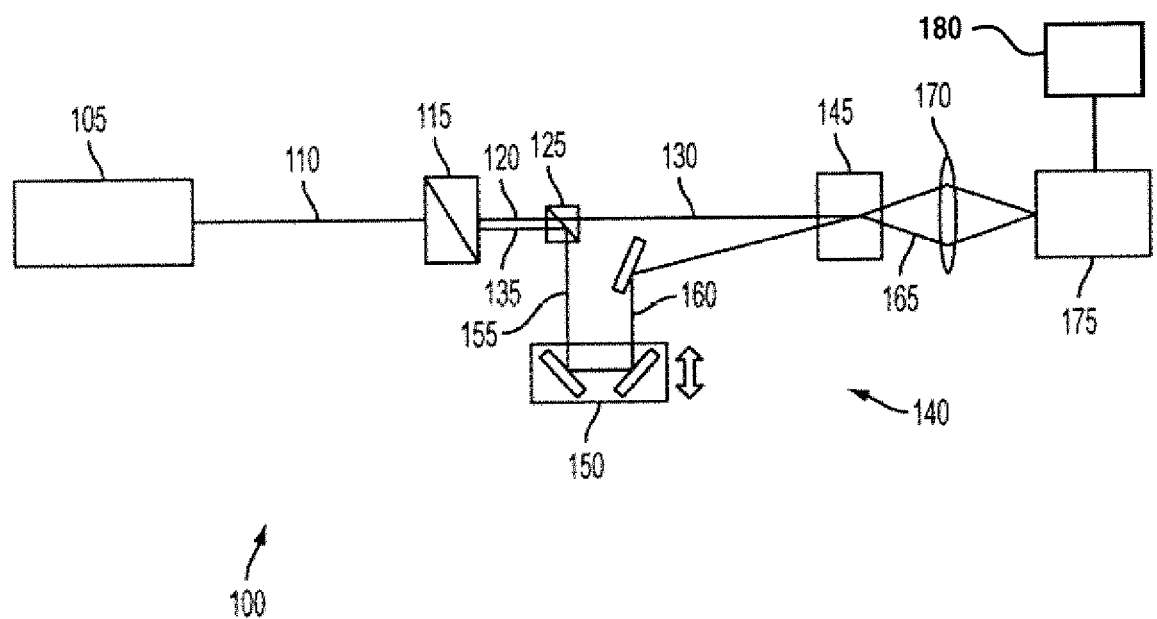
FIG. 1 is a schematic diagram of an embodiment of the present invention.

FIG. 1 is a schematic diagram of a stand-off detection and characterization embodiment 100 according to the present invention. Laser 105 produces an ultraviolet (UV) light pump beam 110 with a wavelength of, by way of non-limiting example, 389 nanometers (nm). Pump beam 110 is directed to adjustable nonlinear crystal 115. Adjustable nonlinear crystal 115 is preferably constructed of beta barium borate (BBO), although other nonlinear crystal materials may be used. Adjustable nonlinear crystal 115 converts pump beam 110 into entangled-photon pairs 120 via type-II parametric downconversion. Entangled-photon pairs 120 produced by adjustable nonlinear crystal 115 comprise signal photons 130 and idler photons 135. Signal photons 130 are polarized at 90° to idler photons 135. Entangled-photon pairs 120 are directed to polarizing beam splitter (PBS) 125, which separates signal photons 130 from idler photons 155 according to polarization. Signal photons 130 are directed to sample material 145, and idler photons are directed to adjustable delay 140. Adjustable delay 140 includes movable mirror set 150. Idler photons 135 leaving adjustable delay 140 are directed to sample material 145, where they join signal photons 130. Sample material 145 may absorb signal photons 130 and idler photons 135 by way of entangled-photon absorption. Fluorophotons 165 released by sample material 145 in response to entangled-photon absorption are gathered by collector 170 and directed to detector 175. Preferably, collector 170 has a relatively large aperture. Band-pass, high-pass, or low-pass filtering may be incorporated into detector 175 to select particular fluorophotons and suppress background noise. Detector 175 is preferably a high-efficiency low-noise single-photon detector, such as, by way of non-limiting example, a photo-multiplier tube or an avalanche photodiode. Detector 175 is placed in the image plane to detect fluorophotons 165 and feed corresponding data to computer 180. Such data may comprise, by way of non-limiting example, one or more electrical signals indicative of detection.

Stand-off detection and characterization embodiment 100 is used to analyze spectroscopic properties of sample material 145. More particularly, by manipulating parameters associated with entangled photons and monitoring whether sample material 145 fluoresces in response to being bombarded by these photons, stand-off detection and characterization embodiment 100 ascertains certain spectroscopic properties of sample material 145. As discussed below in reference to FIGS. 2 and 3, entangled-photon parameters that may be usefully manipulated in embodiments of the present invention include entanglement time and interbeam delay. Standard electronic hardware or software (e.g., 180) is used to gather relevant entangled-photon parameter information and fluorescence observations and thereby compute derived spectroscopic information. Specifics of this derivation and the types of spectroscopic information that may be determined are presented in detail below in reference to FIG. 6.

Figure 2:
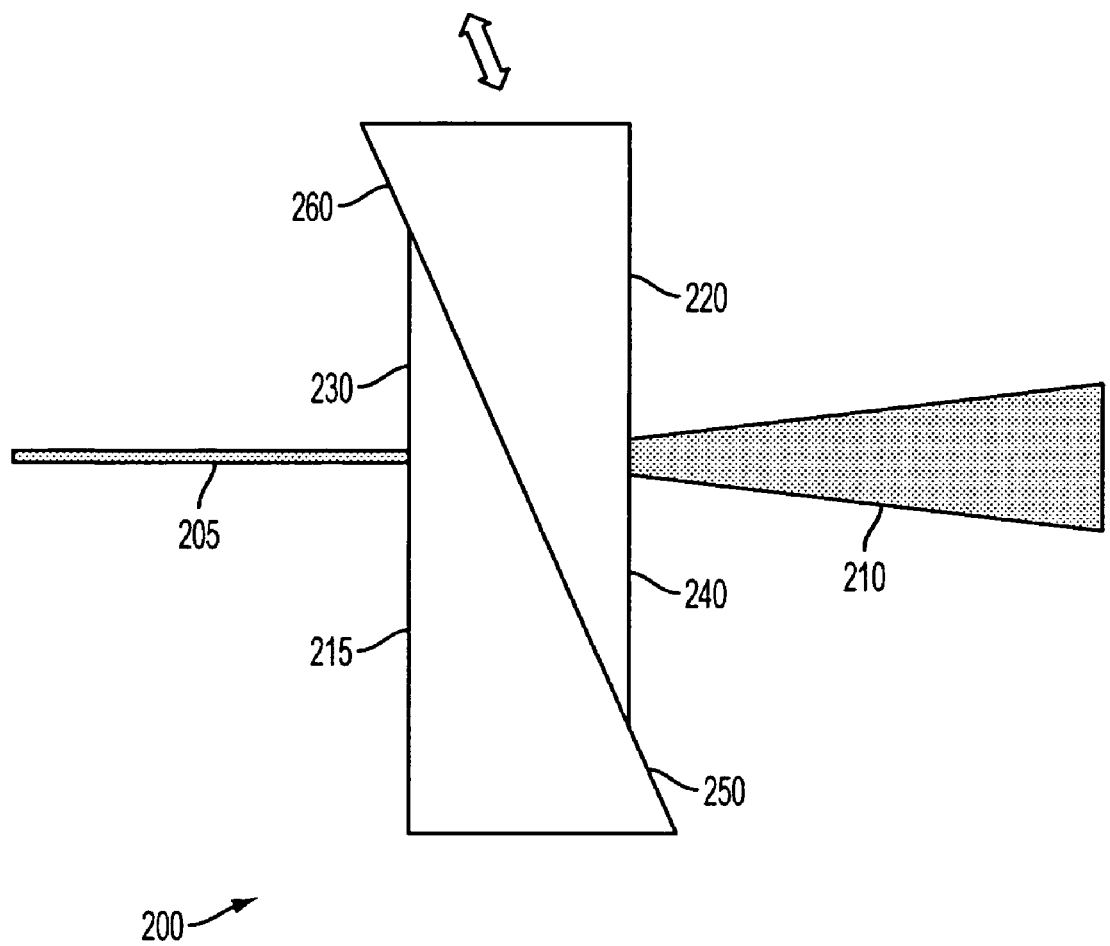
FIG. 2 is a schematic diagram of an adjustable nonlinear crystal according to an embodiment of the present invention.

FIG. 2 is a schematic diagram of an exemplary adjustable nonlinear crystal 200 according to an embodiment of the present invention. Adjustable nonlinear crystal 200 may be used in the embodiment of FIG. 1 in the capacity of adjustable nonlinear crystal 115. Adjustable nonlinear crystal 200 includes two wedge-shaped halves 215, 220. Nonlinear crystal half 215 is fixed relative to incoming photon beam 205. Nonlinear crystal half 215 abuts nonlinear crystal half 220 along their respective hypotenuse faces 260, 250 with an index-matching fluid disposed there between. Nonlinear crystal half 215 is translatable with respect to nonlinear crystal half 220. Accordingly, adjustable nonlinear crystal 200 is capable of being configured so as to have different effective widths. Incoming photon beam 205 preferably enters adjustable nonlinear crystal 200 perpendicular to entrance face 230 of nonlinear crystal half 215. Entangled photons 210 exit adjustable nonlinear crystal through exit face 240 of nonlinear crystal half 220. Entrance face 230 and exit face 240 of nonlinear crystal halves 215, 220, respectively, are preferably parallel, regardless of the translation positions of nonlinear crystals halves 215, 220 with respect to each-other. The effective thickness of adjustable nonlinear crystal 200 may be ascertained using, by way of non-limiting example, interferometry. Reporting logic capable of determining the effective thickness of adjustable nonlinear crystal 200 is operatively coupled with a computer.

Adjustable nonlinear crystal 200 is used to produce entangled photons with a known entanglement time. Entanglement time is an entangled photon parameter that depends on the thickness of the nonlinear crystal that produces the entangled photons. Typically denoted $T_e$, entanglement time may be computed as, by way of non-limiting example, $T_e = DL/2$, where D is the difference in inverse group velocities of ordinary and extraordinary rays leaving the nonlinear crystal, and L is the length of the nonlinear crystal. By way of non-limiting example, for BBO, the parameter D may be approximated as $D \approx 0.2$ psec/mm, where "psec" denotes picoseconds. Because the effective width of adjustable nonlinear crystal 200 is manipulable, adjustable nonlinear crystal 200 selects the entanglement time of produced entangled photons. Thus, setting various translation positions of adjustable nonlinear crystal halves 215, 220 allows for production of entangled photons with various corresponding entanglement times. The configuration for selecting entanglement time illustrated in FIG. 2 is not meant to be limiting; other techniques and configurations are also contemplated.

Figure 3:
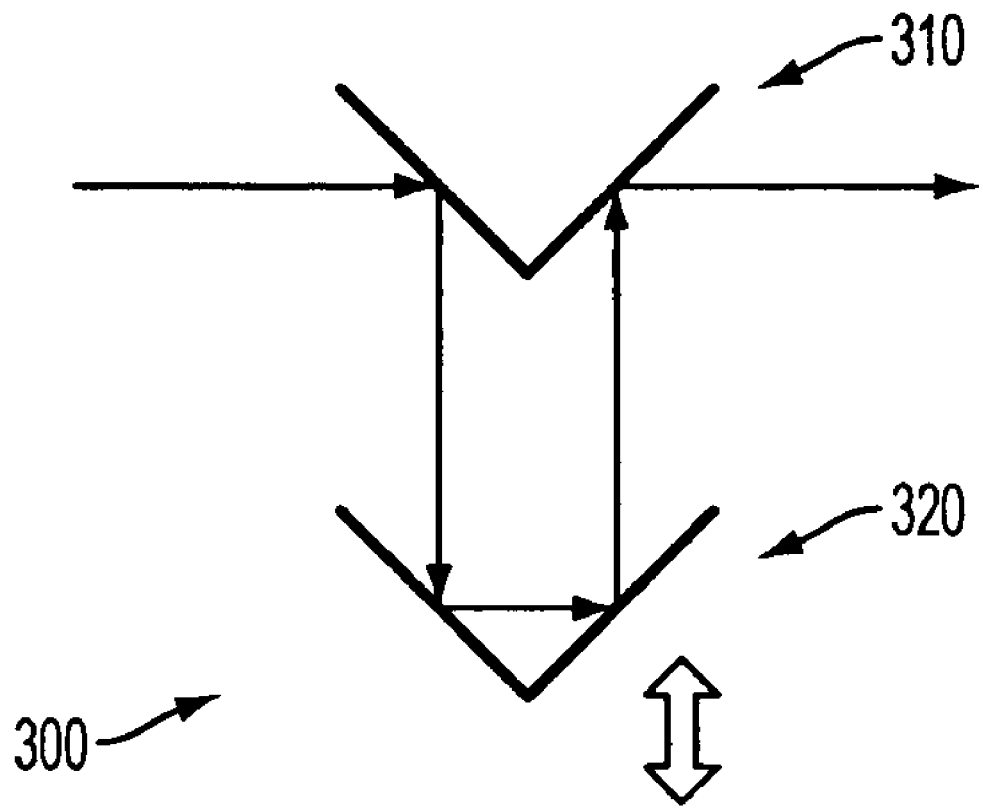
FIG. 3 is a schematic diagram of an adjustable delay according to an embodiment of the present invention.

FIG. 3 is a schematic diagram of an adjustable delay device 300 according to an embodiment of the present invention. Adjustable delay 300 may be used in the embodiment of FIG. 1 in the capacity of adjustable delay 140. Adjustable delay 300 includes a first mirror set 310 and a second mirror set 320. Second mirror set 320 is translatable with respect to first mirror set 310. By manipulating the distance between first mirror set 310 and second mirror set 320, the optical path length traveled by photons entering adjustable delay 300 may accordingly be manipulated. In operation, a photon beam entering adjustable delay 300 encounters first mirror set 310 and is diverted to second mirror set 320. Second mirror set 320 reflects the photon beam back to first mirror set 310, which returns the photon beam to the line defined by the entering photon beam. The increased distance provided by adjustable delay may be monitored using, by way of non-limiting example, interferometry. The particular arrangement for delaying photons disclosed by FIG. 3 is not meant to be limiting; other apparatuses and configurations for delaying photons are also contemplated.

Adjustable delay 300 is used to select an interbeam delay parameter of entangled photons. More particularly, when used in an embodiment of the present invention, adjustable delay 300 interposes a temporal delay between constituent photons of an entangled photon pair. This delay, generally denoted by τ, is referred to as the "interbeam delay" associated with the entangled photons. That is, the interbeam delay of an entangled photon pair is the delay induced by lengthening the optical path of one of the signal or idler photon relative to the optical path length of the other of the signal or idler photon.

Figure 4:
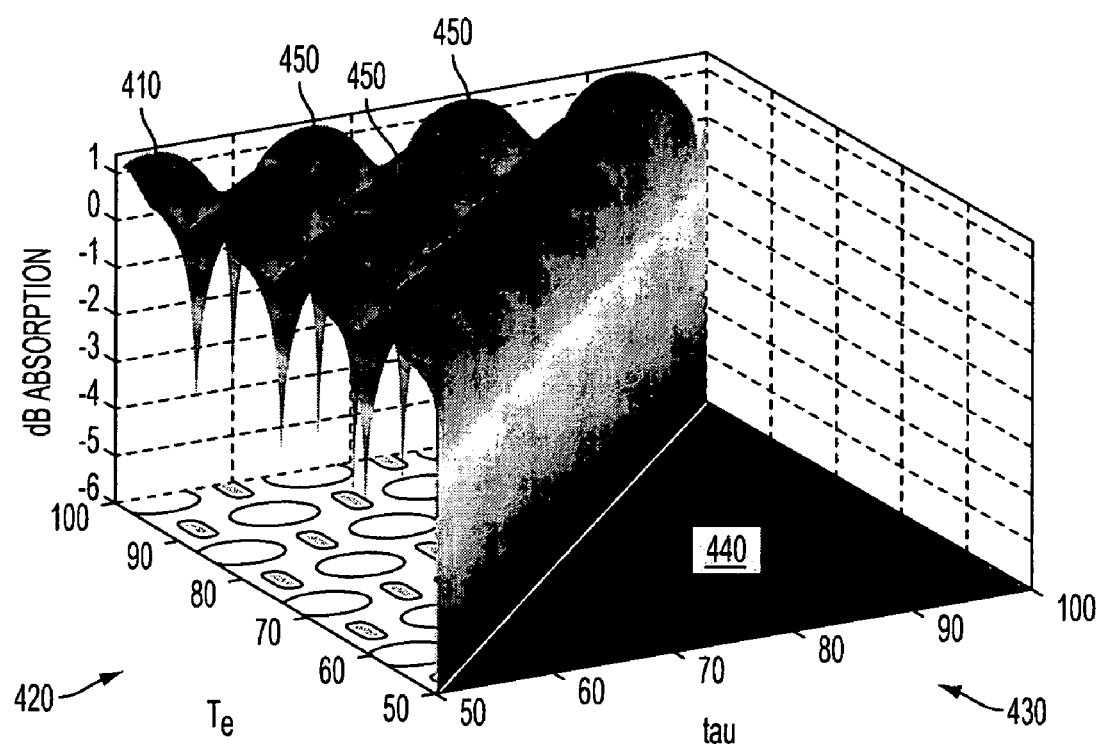
FIG. 4 is a plot of entangled-photon absorption in hydrogen as a function of interbeam delay and entanglement time according to an embodiment of the present invention.

FIG. 4 is a plot of entangled-photon absorption by hydrogen as a function of interbeam delay and entanglement time according to an embodiment of the present invention. More particularly, FIG. 4 depicts entangled photon absorption 410 measured in decibels (dB) as a function of entanglement time $T_e$ 420 and interbeam delay τ 430. As is apparent from FIG. 4, entangled photon absorption is periodic in each of entanglement time and interbeam delay. Additionally, entangled photon absorption is essentially nonexistent, as represented by portion 440, whenever the interbeam delay 430 is greater than the entanglement time 420. Thus, embodiments of the present invention generally ensure that entanglement time 420 is greater than interbeam delay 430.

Embodiments of the present invention generally seek to manipulate entanglement time and interbeam delay so as to maximize entangled photon absorption by the sample material. FIG. 4 illustrates that in the case of hydrogen, there are many possible combinations of entanglement time and interbeam delay that maximize entangled photon absorption, e.g., 450. The entanglement time and interbeam delay of a set of entangled photons are typically manipulated as disclosed above in reference to FIGS. 2 and 3, respectively. Maximizing entangled photon absorption generally maximizes detectible fluorescence, which is in turn used to derive spectroscopic properties of the sample material as described in detail below in reference to FIG. 6. Note however, that either or both of entanglement time and interbeam delay may be manipulated according to embodiments of the present invention. Note also that entangled-photon absorption need not be maximized for embodiments of the present invention to successfully operate. That is, a less-than-maximal amount of entangled-photon absorption suffices in some embodiments of the present invention.

Figure 5:
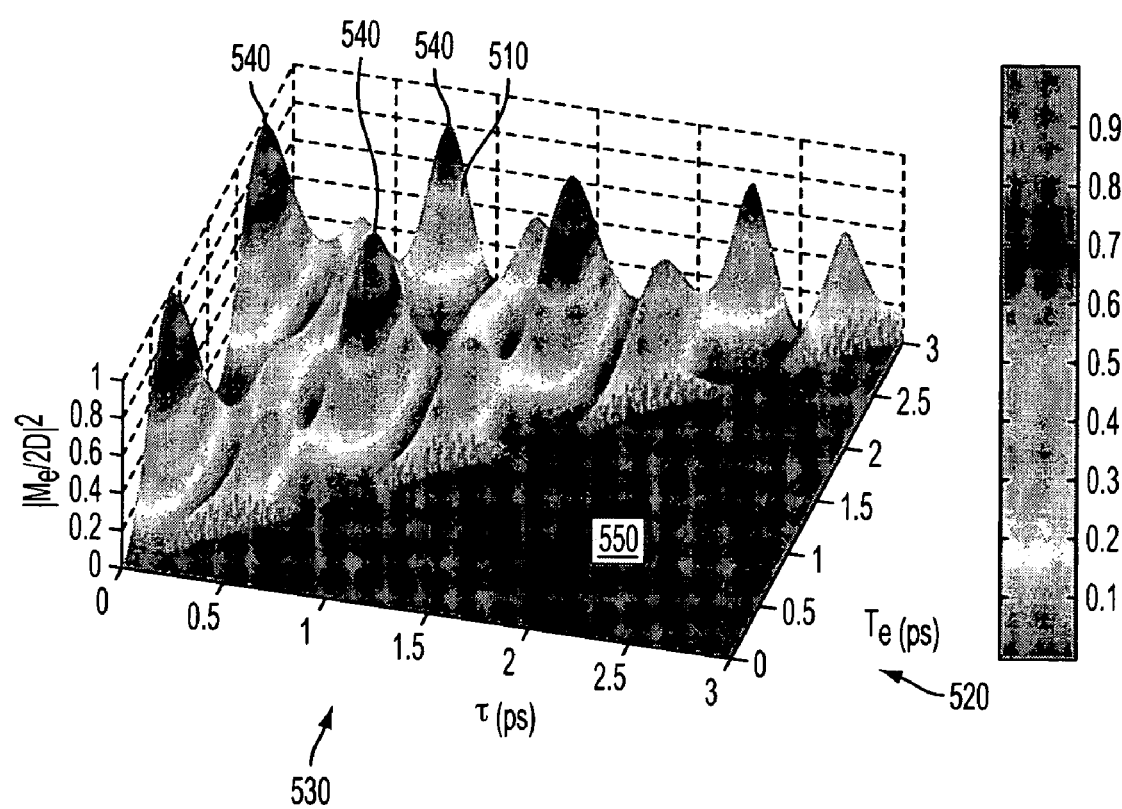
FIG. 5 is a plot of entangled-photon absorption as a function of interbeam delay and entanglement time for rubidium according to an embodiment of the present invention.

FIG. 5 is a plot of entangled two-photon absorption (ETPA) as a function of interbeam delay and entanglement time for rubidium-87 ($^{87}$Rb) according to an embodiment of the present invention. More particularly, FIG. 5 depicts the magnitude squared of the quantum mechanical ETPA matrix element $M_e$ divided by a scaling factor 2D for $^{87}$Rb as a function of entanglement time and interbeam delay. In general, an ETPA matrix element is indicative of the ability of a material to absorb entangled-photon pairs. As illustrated by FIG. 5, there are several combinations of entanglement time and interbeam delay that maximize entangled photon absorption, e.g., local maxima 540.

Figure 6:
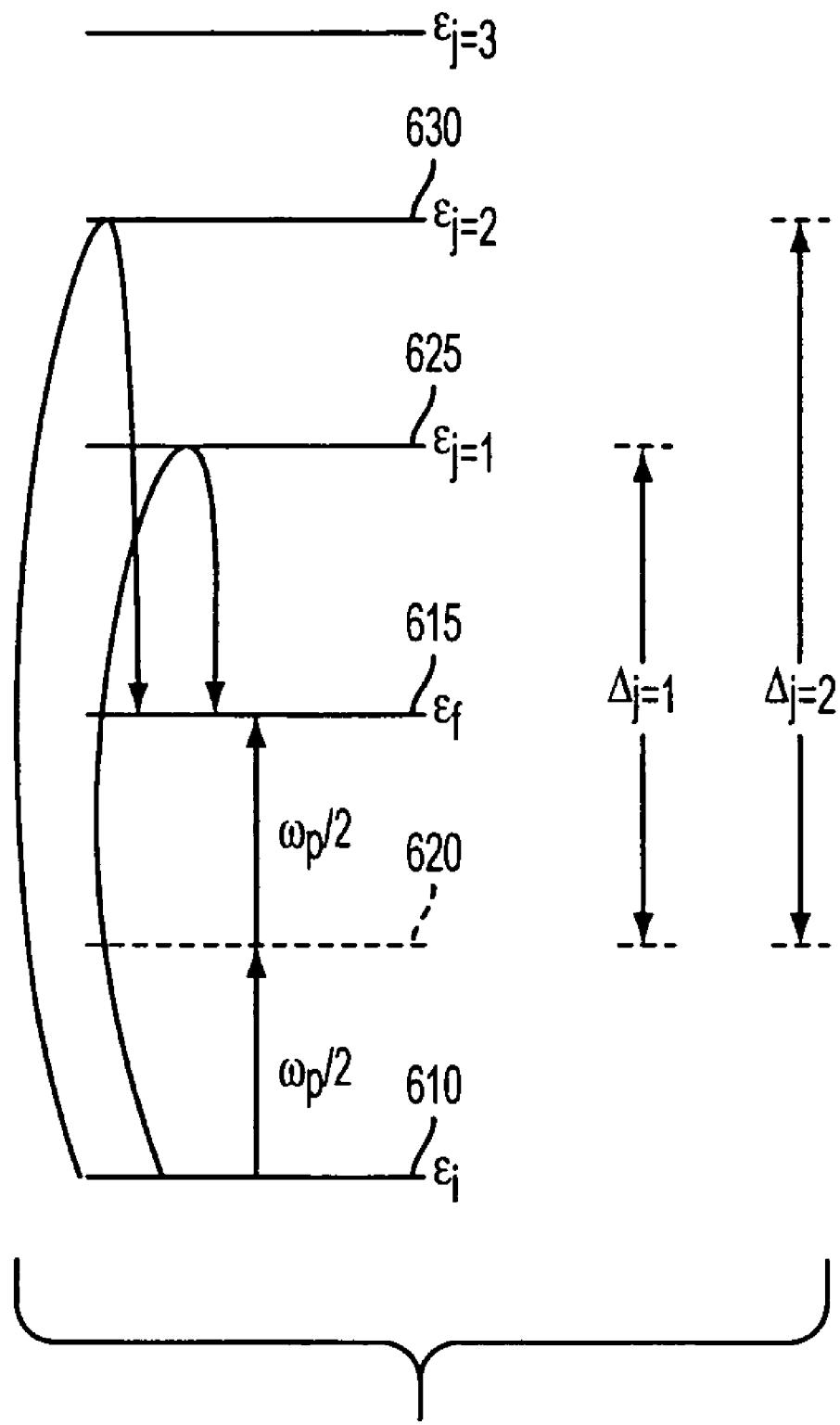
FIG. 6 is a schematic diagram illustrating energy levels in an atom or molecule undergoing entangled two-photon absorption according to an embodiment of the present invention.

FIG. 6 is a schematic diagram illustrating energy levels in a sample material undergoing ETPA according to an embodiment of the present invention. Each solid horizontal line segment 610, 615, 625, 630 represents an electron energy level in the material. Initial energy state $\epsilon_i$ 610 represents the energy level of the material before ETPA. Final energy state $\epsilon_f$ 615 represents the post-ETPA energy level of the material, just before it fluoresces. The entangled photons absorbed by the material as represented in FIG. 6 originate from a down-conversion process in a nonlinear crystal driven by a pump laser of frequency ωp. Thus, the sum of the frequencies of the signal photon and idler photon in such an entangled photon pair is $\omega_p$. For degenerate signal and idler photons, dotted line 620 represents an energy level corresponding to one-half of $\omega_p$. The final energy level $\epsilon_f$ 615 minus the initial energy level $\epsilon_i$ equals the total energy of the entangled photon pair, $\omega_p$.

Immediately after absorbing the entangled photons, the material's electronic state makes virtual transitions through energy levels 625, 630, which are higher than the total energy of the entangled photons. Such energy levels are denoted by $\epsilon_j$ and referred to as virtual states. An embodiment of the present invention is capable of discerning properties of the material, including the material's identity, from spectroscopic information related to such virtual states. One such distinguishing property, discussed further below, is an energy difference between such virtual states $\epsilon_j$ and the ground state $\epsilon_i$ of the material.

Toward explaining how an embodiment of the present invention derives spectroscopic information, an ETPA cross-section theory is disclosed presently. An ETPA cross-section tells how likely a material is to absorb entangled-photon pairs. The larger the ETPA cross-section, the more strongly a material absorbs entangled-photon pairs. The ETPA cross-section of material as a function of entanglement time and interbeam delay may be represented as, by way of non-limiting example:

$$\sigma_e(T_e, \tau) = \frac{\pi \omega_p^2}{16 A_e T_e} \delta(\varepsilon_f - \varepsilon_i - \omega_p) s(T_e, \tau). \tag{1}$$

In equation (1), $\sigma_e$ represents the ETPA cross section, $T_e$ represents the entanglement time, τ represents the interbeam delay, $\omega_p$ represents the pump laser frequency, and $A_e$ represents the entanglement area. Entanglement area is a quantity associated with the region in a nonlinear crystal in which a single photon gives rise to two entangled photons. The entanglement area may be approximated as, by way of non-limiting example: $A_e \approx \lambda_s \lambda_i / [\sin(\theta_s) \sin(\theta_i)]$, where $\lambda_s$, $\lambda_i$ are the wavelengths of the signal and idler photon, respectively, and $\theta_s$, $\theta_i$ are the opening angles of the signal photon and idler photon beams, respectively. The term $s(T_e, \tau)$ in equation (1) contains spectroscopic information. This term may be written as, by way of non-limiting example:

$$s(T_e, \tau) = \left| \sum_j A_j (2 - e^{-i\Delta_j(T_e - \tau)} - e^{-i\Delta_j(T_e + \tau)}) \right|^2. \tag{2}$$

In equation (2), the symbol $A_j$ is defined as, by way of non-limiting example, the ratio of the dipole transition matrix element $D_j$ to the energy difference $$\Delta_j = \varepsilon_j - \varepsilon_i - \frac{\omega_p}{2}$$

for the transition $|\epsilon_i\rangle \to |\delta_j\rangle \to |\epsilon_f\rangle$ as illustrated by FIG. 6. By way of illustrative, non-limiting example, for equation (2), line widths are assumed to be small ($T_e \kappa_j \ll 1$). Averaging equation (2) over several entanglement times yields, by way of non-limiting example:

$$\bar{s}(\tau) = 4\sum_{j,k} A_j^* A_k + 2\sum_j |A_j|^2 (1 + \cos[2\Delta_j \tau]). \quad (3)$$

The symbols of equation (3) are as described above in reference to equations (1) and (2). The symbol * denotes Hermitian conjugation. Equation (3) is periodic in $\tau$ with a period of $2\Delta_j$. Fourier transforming equation (3) with respect to $\tau$ yields, by way of non-limiting example:

$$\hat{\bar{s}}_0(\omega) \equiv \int \bar{s}(\tau) e^{i\omega\tau} d\tau \quad (4)$$

$$= \left(4\sum_{j,k} A_j^* A_k + 2\sum_j |A_j|^2\right) \int e^{i\omega\tau} d\tau + 2\sum_j |A_j|^2$$

$$\int (\cos[2\Delta_j \tau]) e^{i\omega\tau} d\tau$$

$$= \left(4\sum_{j,k} A_j^* A_k + 2\sum_j |A_j|^2\right) \delta(\omega) +$$

$$\sum_j |A_j|^2 (\delta(\omega + 2\Delta_j) + \delta(\omega - 2\Delta_j)).$$

Equation (4) reveals a spectrum with a peak at zero frequency and peaks symmetrically located at $\pm 2\Delta_j$. Thus, embodiments of the present invention may determine $\Delta_j$ by locating peaks in a plot of equation (4). The amplitudes of the symmetric peaks are represented by $$\frac{D_j^* D_j}{\Delta_j^2}.$$

The transition matrix elements, $D_j$, are of the form $D_j \equiv \langle \epsilon_j | d | \epsilon_j \rangle$ $\langle \epsilon_j | d | \epsilon_i \rangle$, with $\vec{d} \equiv \vec{p} \cdot \hat{e}$ the electric dipole operator for the transitions $|\epsilon_j\rangle \rightarrow |\epsilon_j\rangle$ and $|\epsilon_i\rangle \rightarrow |\epsilon_j\rangle$, where $\vec{p}$ is the momentum operator and $\hat{e}$ a unit vector.

Thus, an embodiment of the present invention, such as that depicted above in reference to FIG. 1, determines spectroscopic information of a sample material by exploiting properties of equations (1)-(4). First, the embodiment directs entangled photons having known entangled-photon parameter values at the sample material. The parameters may be any, or a combination of, entanglement time, interbeam delay, and polarization. The values of these parameters may be scanned in a discrete or continuous fashion. If the embodiment is directed to detecting a particular material, the parameter values may have a limited domain. Second, the embodiment gathers data relating to observed fluorescence and the parameters of the associated incident entangled photons. The embodiment then constructs a data structure representation of observed fluorescence as a function of entangled-photon parameters. This function corresponds with equation (2) above. This, and the other functions subsequently described, are preferably stored as conventional data structures.

Third, if appropriate, values of entanglement time are averaged out, leaving a function of a single variable (e.g., interbeam delay). The resulting function corresponds with equation (3) above. Fourth, this function is Fourier transformed to yield a function whose domain is energy (equivalently, frequency). This function corresponds with equation (4) above and represents a spectral analysis. This function may be stored and used to identify and characterize the material. Alternately, or in addition, by inspecting a plot of this function for peaks, embodiments of the present invention ascertain energy difference values $\Delta_j$. These values comprise spectroscopic information that is valuable in its own right. In particular, embodiments of the present invention may use these values to identify and characterize the sample material. Fifth, embodiments of the present invention may further process or analyze the spectral analysis function or the functions built from observed data and corresponding to equations (2) and (3) to derive yet more spectroscopic information. Such information includes the material's energy level difference $\epsilon_j - \epsilon_i$. Because the energy difference $\Delta_j$ is a function of cop, which is known, as well as $\epsilon_j - \epsilon_i$, embodiments of the present invention may determine this latter quantity once $\Delta_j$ is known. Sixth, the spectroscopic information obtained by observation is compared with pre-stored spectroscopic information in order to identify and characterize the material. Any of the spectroscopic information discussed herein may be used for such a comparison.

Embodiments of the present invention are capable of identifying materials by comparing observed properties with properties stored in a pre-formed database. The database information may be gathered by performing laboratory analysis of materials of interest. Such a database acts as a storehouse of material "fingerprints," which may be used to identify an unknown sample based on its observed spectroscopic properties. A match between stored properties and observed properties yields a material identification. Such a database preferably includes spectral analysis functions, energy differences $\Delta_j$, and energy level differences $\epsilon_j - \epsilon_i$, for a variety of materials. These data may further include shape information of fluorescence-response curves. More particularly, the database preferably includes representations of $\Delta_j$, $\epsilon_j - \epsilon_i$, and other spectroscopic properties, as functions of entanglement time, interbeam delay, and other entangled-photon parameters. Such representations are preferably stored as conventional data structures. These representations may be compared with material responses to multiple entangled-photon bombardments. Such comparisons allow for matching "shapes" of various response curves, instead of matching single point responses.

Another quantity that embodiments of the present invention may ascertain is the magnitude of transition matrix element $D_j$. This can be seen by computing the second derivative of equation (3) with respect to $\tau$ prior to Fourier transforming. The second derivative of equation (3) may be represented as, by way of non-limiting example:

$$\frac{\partial^2 \bar{s}(\tau)}{\partial \tau^2} = -8 \sum_j D_j^* D_j \cos[2\Delta_j \tau]. \quad (5)$$

Equation (5) is then Fourier transformed to yield, by way of non-limiting example:

$$\hat{\bar{s}}_1(\omega) \equiv \int \frac{\partial^2 \bar{s}(\tau)}{\partial \tau^2} e^{i\omega\tau} d\tau \qquad (6)$$

$$= -8 \sum_j D_j^* D_j \int \cos[2\Delta_j \tau] e^{i\omega\tau} d\tau$$

$$= -4 \sum_j D_j^* D_j (\delta(\omega + 2\Delta_j) + \delta(\omega - 2\Delta_j)).$$

Equation (6) contains transition matrix magnitude information. The graph of equation (6) represents spectral information, has no d.c. (zero frequency) component, and possesses symmetrically-located peaks. The amplitude of each peak is proportional to the magnitude of the transition matrix element $D_j$ for the given $\Delta_j$. Accordingly, transition matrix magnitude information is also preferably included in the material "fingerprint" database (e.g., transition matrix magnitude as a function of one or more entangled-photon parameters). Such information provides additional data that may be used to identify a sample.

Note that embodiments of the present invention are capable of ascertaining sample material spectroscopic information using only a single pump laser frequency. This is in contrast with conventional spectroscopy in which the frequency of probing radiation varies and intermediate state properties correlate only with probe radiation frequency. Embodiments of the present invention may ascertain a plethora of spectroscopic material information by using a single pump frequency and varying one or more entangled-photon parameter(s). Such parameters may include entanglement time and interbeam delay, as discussed above, and also preferably include others, such as constituent photon polarization and relative energy distribution between signal and idler photons (or between multiple photons for multiply-entangled photon embodiments). Nevertheless, in some embodiments of the present invention, pump laser frequency may also be varied.

Figure 7:
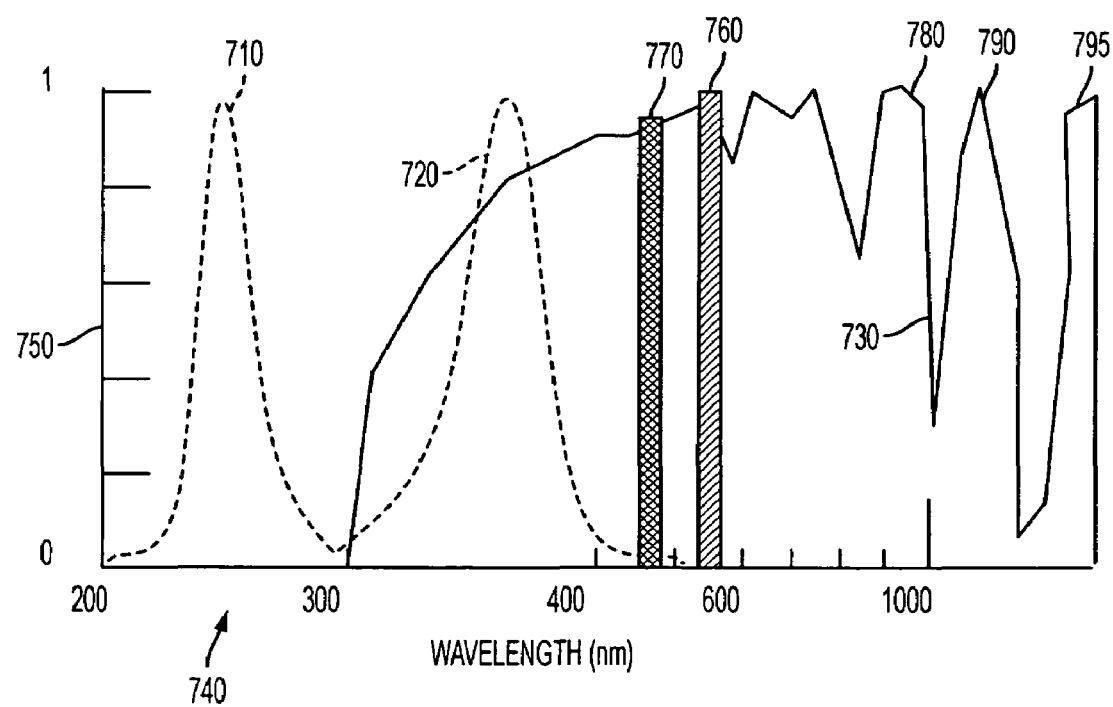
FIG. 7 is a plot of typical biological material absorption and fluorescence curves together with an atmospheric transmittance curve according to an embodiment of the present invention.

FIG. 7 is a plot of typical biological material absorption and fluorescence curves together with an atmospheric transmittance curve according to an embodiment of the present invention. The x-axis 740 represents photon wavelength measured in nm. Curve 710, with a peak at approximately 240 nm, represents photon absorption probability for biological material as a function of photon wavelength. Thus, for curve 710, the y-axis 750 represents absorption probability. Curve 720, with a peak at about 360 nm, represents biological material fluorescence emissions. For curve 720, the y-axis 750 represents fluorescence probability according to fluorophoton wavelength. Curve 730 represents atmospheric transmittance as a function of photon wavelength. Thus, for curve 730, the y-axis 750 represents atmospheric transmittance.

FIG. 7 also illustrates the limitations of traditional spectroscopic techniques for long-range biological material identification. As depicted in FIG. 7, biological materials typically have an excitation band in the UV spectral range (e.g., 220-300 nm). This band generally corresponds with the absorption band of aromatic amino acids found in biological organisms, such as tryptophan, phenolalanine and tyrosine. However, atmospheric transmittance for this spectral range is very low, and for single photons, biological material absorption and atmospheric transmission windows do not in general overlap. Consequently, traditional techniques for long-range standoff detection and characterization of biological materials are limited because the atmosphere absorbs nearly all of the UV light before it reaches the biological material. This phenomenon makes non-entangled photon spectroscopic techniques for detection of UV-induced biological material fluorescence at long ranges impossible.

In contrast, embodiments of the present invention overcome these obstacles. By using two entangled photons instead of a single photon to excite biological materials, standoff detection and characterization range is greatly improved. In particular, instead of UV photons, embodiments of the present invention use entangled-photon pairs produced from single UV photons for biological or other material detection and characterization. Such entangled-photon pairs may be produced from UV photons such that their individual wavelengths are both in the visible light range. This is a consequence of conservation of energy, which states that the sum of the constituent entangled photon's energies must equal the energy of the photon from which they were derived. By way of non-limiting example, a 255 nm UV photon may be used to produce an entangled photon pair consisting of a 550 nm photon 760 and 475 nm photon 770, both of which are readily transmitted by the atmosphere.

Moreover, the atmosphere is much more transparent to visible photons than it is to UV photons. Such entangled-photon pairs produced from UV photons are in general readily absorbed by biological materials. Thus, compared with random UV photons, entangled-photon pairs derived from UV photons travel farther in the atmosphere while retaining the ability to excite biological materials to fluorescence. In this manner, entangled photons having favorable characteristics for atmospheric transmission may be produced and used to characterize materials. Embodiments of the present invention may be used to identify and characterize materials at ranges of less than one kilometer, several kilometers, several tens of kilometers, or several hundreds of kilometers. The ability to identify and characterize materials at such ranges is particularly useful when the material under analysis may be hazardous.

Other advantages of using entangled-photon pairs also exist. For example, entangled photons produced from a high-energy (e.g., UV) photon are safer than a single high-energy photon. UV light is dangerous to the human eye, while entangled photons may be produced from a UV photon such that both constituent photons are harmless to the human eye. Additionally, lower-energy photons are less detectable, which allows for covert material detection and characterization where required.

An embodiment of the present invention may select entangled photons with constituent photons' frequencies particularly suited for travel through the atmosphere with little loss. By way of non-limiting example, FIG. 7 depicts several transmittance peaks, e.g., 780, 790, 795. Such an embodiment may generate entangled photons whose constituent photons' frequencies lie in the domain of one or more of such peaks. Entangled photons consisting of such constituent photons are thus specially suited for atmospheric transmittance. Atmospheric transmittance may be measured for each situation, and the entangled photons selected accordingly, to allow for remote material identification and characterization using photons particularly suited for transmittance according to local atmospheric characteristics.

Thus, entangled-photon pairs may be used to excite materials at distances far greater than those available from conventional techniques. Spectroscopic information may accordingly be gained using embodiments of the present invention at distances that were previously intractable. Note that the techniques disclosed herein are not limited to use on biological materials; any material, whether organic or inorganic, may be analyzed.

Figure 8:
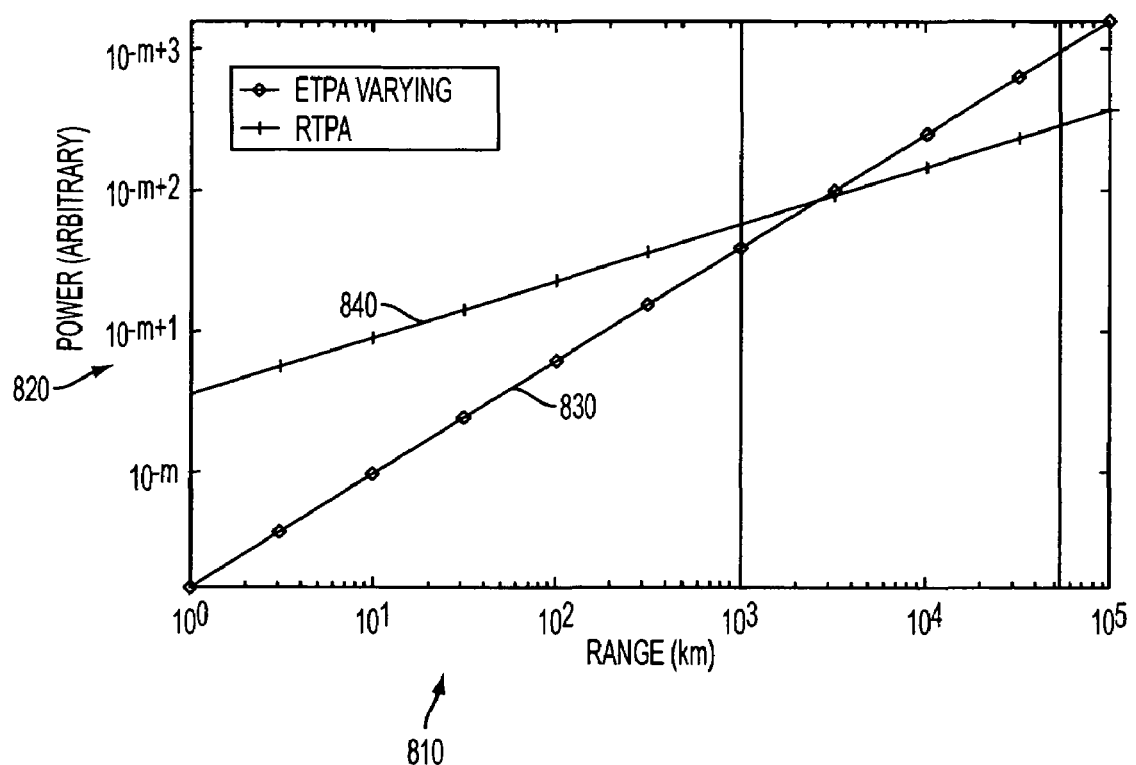
FIG. 8 is a plot of required power as a function of range for both entangled and random photons according to an embodiment of the present invention.

FIG. 8 is a plot of required power as a function of range for both entangled and random photons according to an embodiment of the present invention. In particular, the x-axis 810 represents range in kilometers, and the y-axis 820 represents power in arbitrary units (thus the y-axis represents orders of magnitude of power). Curve 840 represents the power required to transmit random photons through the atmosphere. Curve 830 represents the power required to transmit entangled photons through the atmosphere. As is apparent from FIG. 8, appropriately-configured entangled photons require less power to transmit through the atmosphere up to ranges on the order of 1000 kilometers. Thus, for long-range applications, entangled photons are superior to random photons.

Entangled-photon-production power requirements are analyzed presently. The number of received photons generally depends on at least incident flux, dwell time $T_d$ (the time spent bombarding the material at, and detecting fluorophotons from, a particular location), the number of target molecules $N_t$, the fluorescence efficiency $E_f$ (typically a few percent) and the collection efficiency $E_c$. Incorporating these factors, the number of collected photons $N_c$ may be represented as, by way of non-limiting example:

$$N_c = T_d N_t R_{TPA} E_f E_c. \quad (7)$$

In equation (7), $R_{TPA}$ represents a two-photon absorption rate, which may be either random or entangled. Assume for purposes of illustration and by way of non-limiting example that the material to be detected and characterized is in the form of a cloud. Given the depth l of the cloud, the area $A_b$ of the beam at the cloud, and the density $\rho$ of the cloud, we have $N_t = l A_b \rho$. Assuming, for the purpose of illustration, perfect detection modules (actual efficiencies are about 0.5), for a collection aperture of area $D^2$, the collection efficiency at range R may be estimated as, by way of non-limiting example:

$$E_c \sim 3D^2/4\pi R^2 \sim D^2/R^2. \quad (8)$$

The beam spot area for biphotons of wavelength $\lambda$ at range R may be estimated at, by way of non-limiting example:

$$A_b \sim (\lambda R/D)^2. \quad (9)$$

Combining equations (7), (8), and (9) yields:

$$\begin{aligned} N_c &= T_d l A_b \rho R_{TPA} E_f E_c \\ &= T_d l \left(\frac{\lambda R}{D}\right)^2 \rho R_{TPA} E_f \left(\frac{D}{R}\right)^2 \\ &= T_d l \lambda^2 \rho R_{TPA} E_f \end{aligned} \quad (10)$$

The two-photon production rate may be estimated from equation (10) as, by way of non-limiting example:

$$R_{TPA} = \frac{N_c}{T_d l \lambda^2 \rho E_f}. \quad (11)$$

By selecting a value of $N_c$ that corresponds with a desired detection level, it is possible to estimate how much output power is needed to achieve that detection level as a function of range. The transmitted power P is assumed by way of non-limiting example to be un-pulsed. The energy of each transmitted photon is $E_\lambda = hc/\lambda = h\epsilon_f/2$ and the flux density may be written as, by way of non-limiting example:

$$\phi = \frac{P\lambda}{A_b hc} = \frac{P\lambda D^2}{hc\lambda^2 R^2} = \frac{PD^2}{hc\lambda R^2}. \quad (12)$$

The entanglement area of biphotons as initially generated may be transformed by subsequent optics. The entanglement area at the absorbing molecule thus depends on the distance from the sensor to the target and corresponds with the size of the beam spot at the absorbing molecule. Thus, the power requirement may be estimated as, by way of non-limiting example:

$$P^{ETPA-A_b} \sim \frac{R_{TPA} hc\lambda R^2}{\bar{\sigma}_e D^2} \frac{A_b}{A_e} = \frac{R_{TPA} hc\lambda^3 R^4}{\bar{\sigma}_e A_e D^4}. \quad (13)$$

In equation (13), $\bar{\sigma}_e$ represents the ETPA cross-section, $R_{TPA}$ represents the entangled two-photon absorption rate, and $P^{ETPA-A_b}$ represents the power incident on the material required to achieve the selected $N_c$ value. In contrast, the power required for equivalent random two-photon absorption may be written as, by way of non-limiting example:

$$P^{RTPA} = \frac{hc\lambda R^2}{D} \sqrt{\frac{R_{TPA}}{\bar{\sigma}_e A_e T_e}}. \quad (14)$$

In equation (14), $R_{TPA}$ represents the random two-photon absorption rate.

Figure 9:
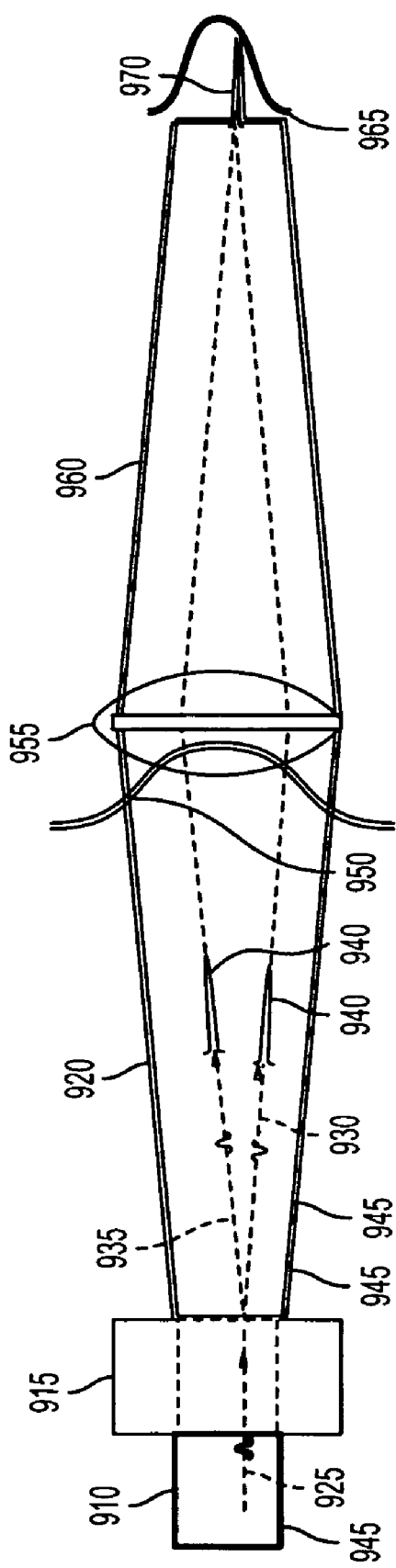
FIG. 9 is a schematic diagram of biphoton propagation according to an embodiment of the present invention.

FIG. 9 is a schematic diagram of biphoton propagation according to an embodiment of the present invention. Pump beam 910 is directed to nonlinear crystal 915, which produces entangled photon beam 920. At the single-photon level, pump beam photon 925 is converted into signal photon 930 and idler photon 935. These individual photons 940 represent coherent wave functions, whereas beams 945 are generally incoherent. The beam waist 950 is generally indicative of entanglement area. Lens 955 focuses divergent entangled photon beam 920 into convergent entangled photon beam 960. Convergent entangled photon beam 960 arrives at image plane 965, which is the location at which signal photon 930 and idler photon 935 are absorbed.

The path of each photon is individually analyzed as follows. Signal photon 930 originates at coordinate $\vec{r}_2$ from the face of nonlinear crystal 915 and is transformed according to, by way of non-limiting example:

$$I(\vec{r}_2) = \int d\vec{r}_1 I(\vec{r}_1) |h(\vec{r}_1, \vec{r}_2)|^2. \quad (15)$$

In equation (15), I represents the signal photon beam intensity at the exit face of nonlinear crystal 915, $\vec{r}_1$ represents the coordinate in image plane 965 of signal photon 930, and h represents the system transfer function for lens 955. An equation analogous to equation (15) obtains for incoherent transformation of idler photon 935. The coherent wave function of the entangled photon pair is transformed as, by way of non-limiting example:

$$\Psi(\vec{r_3},\vec{r_4}) = \int d\vec{r_1} \int d\vec{r_2} \Psi(\vec{r_1}, \vec{r_2}) h(\vec{r_1},\vec{r_3}) h(\vec{r_2},\vec{r_4}). \qquad (16)$$

In equation (16), the parameters are the same as those of equation (15), with the following additions: $\Psi$ represents the biphoton coherent wave function, $\vec{r_3}$ represents the coordinate of idler photon 935 at image plane 965, and $\vec{r_4}$ represents the coordinate of signal photon 930 at image plane 965. The entanglement area for the photons depicted in FIG. 9 may be computed as, by way of non-limiting example, $A_e = \pi r_e^2$, where $r_e$ is the solution to $|\Psi(r_3, r_4-r_e)|^2 = 1/e$.

Figure 10:
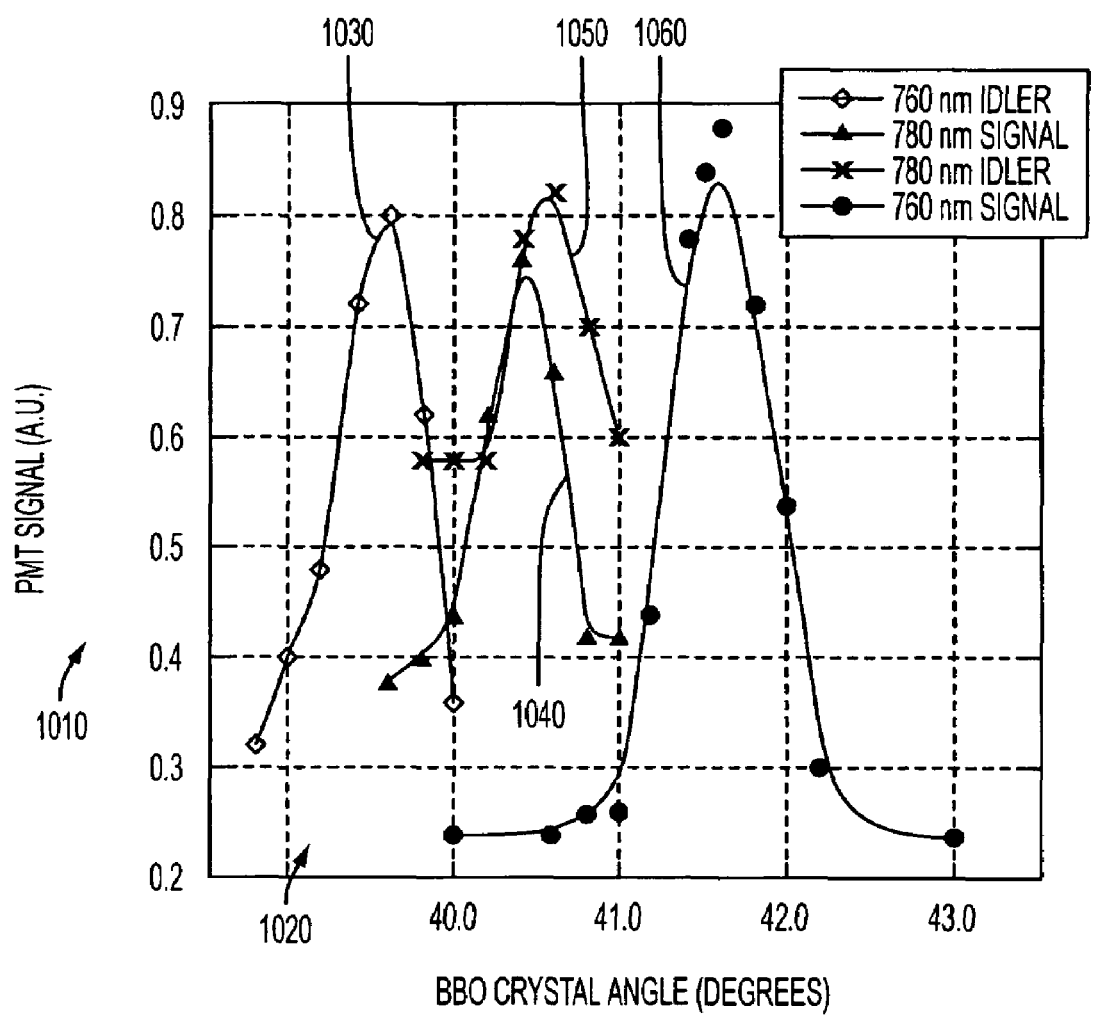
FIG. 10 is a plot of beta barium borate (BBO) production of biphotons with differing constituent photon frequencies as a function of BBO angle.

FIG. 10 is a plot of BBO production of biphotons with differing constituent photon frequencies as a function of BBO angle. The x-axis 1020 represents BBO crystal angle in degrees, and the y-axis represents photomultiplier tube (PMT) readings. The plot illustrates that constituent photons of entangled-photon pairs are available in a variety of wavelengths and may be selected according to BBO crystal angle. As represented by curves 1030 and 1040, 760 nm idler photons and 780 nm signal photons are available at approximately 39.6° and 40.4°, respectively. As represented by curves 1050 and 1060, 780 nm idler photons and 760 nm signal photons are available at approximately 40.5° and 41.5°, respectively.

In one embodiment the present invention requires less probing radiation energy compared with conventional techniques using similar levels of eye-safe radiation. This has the benefit of offering material identification and characterization with reduced material bleaching. In contrast with traditional photon sources, which provide Poisson-distributed photons that arrive randomly and independently, an entangled-photon source according to an embodiment of the present invention provides photons entangled in space and time. Such photons may be configured to arrive simultaneously at a material rather than randomly and independently, thus necessitating lower intensity radiation while achieving a similar degree of absorption. Another advantage of using entangled photons is seen by examining absorption as a function of photon flux. In general, random two-photon absorption by a material for non-entangled photons is proportional to the square of the incident radiation flux. In contrast, entangled-photon absorption by a material is generally linearly proportional to the incident radiation flux. Thus, under low-flux conditions (under the critical flux, i.e., the flux at which random two-photon absorption and ETPA rates are equal), less flux is required of entangled photons when compared with non-entangled photons to achieve the same level of absorption. As a result, less energy is required to probe a material. Material samples that would be bleached by radiation required for conventional techniques may be safely identified and characterized without such bleaching according to an embodiment of the present invention.

Many different materials may be identified and characterized in embodiments of the present invention. Examples of biological materials that may be detected and characterized at long ranges include, by way of non-limiting example, nerve gas (such as sarin), spores (such as anthrax), bacteria, viruses, and organic chemicals. Inorganic materials that may be detected and characterized include, by way of non-limiting example, potentially radioactive materials (such as cobalt, cesium, radium, plutonium, or uranium), chlorine gas, and other materials with tactical significance. Materials may be solid, liquid, gas, aerosolized, or colloids. An embodiment of the present invention may be configured to detect chemical, biological, or potentially nuclear material dispersion (e.g., a so-called "dirty bomb") over large ranges, such as in the upper atmosphere or on the grounds of a government compound.

Embodiments of the present invention may have various configurations of entangled-photon sources and fluorescence detectors. By way of non-limiting example, the entangled-photon source may be at the same physical location as the fluorescence detector, or may be at a different physical location. Either or both of the entangled-photon source and florescence detector may be fixed or mobile, on the ground, in the air, or orbiting the Earth. Either or both of the entangled-photon source and florescence detector may be located on a vehicle, such as a terrestrial motor vehicle or aircraft. Either or both of the entangled-photon source and florescence detector may be located in close proximity to the material to be identified, such as in the same room. For laboratory settings, an embodiment of the present invention may be a single desktop unit. In some embodiments, entangled-photon pairs are sent over optical fiber, and subsequent fluorophoton emissions are detected and analyzed as described herein.

Biphotons of any frequency may be used in embodiments of the present invention. That is, entangled photons may be produced from light of any frequency. In particular, the present invention is not limited to using entangled photons produced from UV light to ascertain spectroscopic properties. Entangled photons may be produced from photons of any frequency consistent with the present invention.

The various calculations, comparisons, and judgments required during operation in order to ascertain spectroscopic properties and identify and characterize materials according to embodiments of the present invention may be accomplished by conventional computer hardware or software. These calculations are preferably performed automatically during the normal course of operation of embodiments of the present invention. By way of non-limiting example, the computations and comparisons associated with equations (1)-(6) used to identify and characterize materials may be performed by appropriately programmed or configured standard computer hardware or software.

Note that the terms "signal" and "idler" may be used interchangeably. More particularly, as used herein, no distinction is drawn between signal photons and idler photons.

By way of elaborating on earlier definitions, entanglement time is a quantity associated with the spread in phase differences between signal photons and associated idler photons. That is, entanglement time relates to the collection of differences in phase between signal photons and associated idler photons produced by an entangled-photon source (e.g., a non-linear crystal). Entanglement time may be, by way of non-limiting example, considered as the average time difference between when ordinary and extraordinary rays leave a nonlinear crystal. Ordinary rays leaving a nonlinear crystal are typically associated with signal photons, and extraordinary rays leaving a nonlinear crystal are typically associated with idler photons. By way of non-limiting example, entanglement time is a function of the length l of a non-linear crystal used to produce the entangled photons, and may be described as $T_e = l(n_o - n_e)/2c$, where $n_o$, $n_e$ are indices of refraction associated with ordinary and extraordinary crystal directions, respectively. By way of non-limiting example, entanglement times on the order of $T_e = 5 \times 10^{-13}$ seconds are possible with a crystal length of 5 mm. These parameters yield an entanglement distance (the distance that light can travel during the entanglement time) of 0.15 mm.

Alternate embodiments of the present invention may calculate entanglement area $A_e$ according to the following, which describes a non-limiting exemplary technique for such computation. It is typically possible to calculate fourth-order correlation height and width coefficients. In the direction defined by the x-axis, and for a given signal photon at location $x_s$, the idler photon in location $x_i$ will generally arrive within $\Delta x$ of $x_s$ (i.e., $x_i = x_s \pm \Delta x$). Similarly, in the z-axis direction, and for a given signal photon at location $z_s$, the idler photon in location $z_i$ will arrive within $\Delta z$ of $z_s$ (i.e., $z_i = z_s \pm \Delta z$). The quantities $\Delta x$ and $\Delta z$ may generally be computed using fourth-order correlation theory. The entanglement area $A_e$ may be derived as the product of $\Delta x$ and $\Delta z$ (i.e., $A_e = \Delta x \Delta z$).

Entangled photons with selected entanglement times may be produced according to a variety of techniques. Instead of adjustable nonlinear crystal 200 of FIG. 2, embodiments of the present invention may use two right parallelepiped nonlinear crystals that are closely spaced apart to produce entangled photons with selected entanglement times. In such embodiments, adjusting the distance between the two nonlinear crystals controls the entanglement time of entangled-photon pairs produced by the crystals. In alternate embodiments of the present invention, a single wedge-shaped nonlinear crystal may be used to produce entangled photons with selected entanglement times. By moving such a crystal relative to the pump laser such that the width through which the pump laser beam passes varies, entangled photons with different entanglement times may be produced. In other alternate embodiments of the present invention, entanglement times of entangled-photon pairs may be selected by spectral filtering. In such embodiments, constituent photons of entangled-photon pairs are selected by choosing the appropriate angle (as described above in reference to FIG. 10) or by optical filtering. Each photon's angle at exiting the crystal depends on the photon's propagation speed through the nonlinear crystal. Because, as discussed above, entanglement time may be considered as the average time difference between when ordinary and extraordinary rays leave the nonlinear crystal, by selecting the angle at which photons appear, embodiments of the present invention effectively select the entanglement time as well.

Other types of entangled photons and techniques for producing them within the scope of the present invention include the following. Those of ordinary skill in the art are capable of producing entangled-photon pairs, triples, etc. By way of non-limiting example, entangled photons may be produced according to types I or II parametric down-conversion. That is, biphotons whose constituent signal and idler photons are orthogonally polarized may be used as well as biphotons whose constituent signal and idler photons are polarized in parallel. For type-I downconversion, signal photons may be separated from idler photons (and recombined with idler photons) using dichroic glass. For both types of downconversion, signal photons and idler photos may be selected as they exit the biphoton source by providing apertures at the appropriate angles. Any non-central symmetric nonlinear crystal, not limited to BBO, may be used. Other ways to produce entangled photons include: excited gasses, materials without inversion symmetry, and generally any properly phase-matched medium. Furthermore, the entangled photons are not limited to any particular wavelength or frequency.

In embodiments of the present invention, evidence of entangled-photon absorption may be of a variety of forms. By way of non-limiting example, entangled-photon absorption may result in fluorescence, phosphorescence, direct electron transfer, or ionization of the absorbing material. Detecting fluorescence, phosphorescence, direct electron transfer, or ionization may be used to detect entangled-photon absorption. Also by way of non-limiting example, avalanche photo-diodes, photo multiplier tubes, or other devices may be used to detect the fluorophotons, ionization, direct electron transfer, or other absorption indicia.

The equations contained in this disclosure are illustrative and representative and are not meant to be limiting. Alternate equations may be used to represent the same phenomena described by any given equation disclosed herein. In particular, the equations disclosed herein may be modified by adding error-correction terms, higher-order terms, or otherwise accounting for inaccuracies, using different names for constants or variables, using different expressions, or accounting for propagation of light through different media. Other modifications, substitutions, replacements, or alterations of the equations may be performed.

The particular optical manipulation devices depicted herein are illustrative and representative and are not meant to be limiting. By way of non-limiting example, apertures, filters, lenses, and particular lasers disclosed herein may be replaced with devices known to those of ordinary skill in the art.

Alternate embodiments of the present invention may delay one photon in various ways. By way of non-limiting example, a length of optical fiber may be inserted into the path of one or both photons. Alternately, sets of mirrors may be used to increase the path length of one or both photons. Other techniques for delaying one or more photons may also be used.

Note that this disclosure follows standard physics notational conventions. By way of non-limiting example, in some places Planck's constant h (and ℏ) and the speed of light c may both considered to be one (1) for the purpose of calculations. This convention allows, inter alia, for common units for frequency and energy, as well as common units for time and distance (e.g., temporal delays may be considered as spatial lengths and vice versa). This notational convention is accounted for after calculations have been performed in order to deduce correct units for application purposes. This disclosure also uses Dirac bracket notation (e.g., $|\psi_i\rangle$), known to those of ordinary skill in the art, to denote quantum states.

It is noted that the foregoing examples have been provided merely for the purpose of explanation and are in no way to be construed as limiting of the present invention. While the present invention has been described with reference to certain embodiments, it is understood that the words which have been used herein are words of description and illustration, rather than words of limitation. Changes may be made, within the purview of associated claims, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses.

What is claimed is:

1. A method of determining spectroscopic properties of a material, the method comprising:

producing entangled photons having a known value of at least one entangled photon parameter;

directing the entangled photons having the known value of at least one entangled photon parameter to a material over a distance of at least one kilometer;

observing indicia of entangled photon absorption by the material;

deducing at least one spectroscopic property of the material based on at least the indicia of entangled photon absorption and the known value of at least one entangled photon parameter; and outputting a signal representing the at least one spectroscopic property.

2. The method of claim 1 wherein the at least one entangled photon parameter is selected from the group consisting of: entanglement area, entanglement time, sum frequency, idler photon frequency, interbeam delay, and polarization.

3. The method of claim 1 wherein the at least one spectroscopic property of the material is selected from the group consisting of: at least one energy difference value, at least one transition matrix magnitude, at least one cross section, a spectral analysis function, and at least one energy level difference.

4. The method of claim 1 wherein the at least one spectroscopic property of the material comprises a function of at least one variable, the at least one variable selected from the group consisting of: entanglement area, entanglement time, energy, sum frequency, idler photon frequency, and interbeam delay.

5. The method of claim 1 wherein the material is selected from the group consisting of: a nerve agent, spores, bacteria, viruses, amino acids, a material with a radioactive isotope, and chlorine gas.

6. The method of claim 1 wherein the indicia of entangled photon absorption is selected from the group consisting of: fluorescence, phosphorescence, direct electron transfer, and ionization.

7. The method of claim 1 wherein the material is selected from the group consisting of: a gas, a solid, a liquid, an aerosol, and a colloid.

8. The method of claim 1 wherein the material is an organic chemical.

9. The method of claim 1 further comprising identifying the material by comparing the deduced at least one spectroscopic property of the material with stored spectroscopic data.

10. The method of claim 1 wherein the step of producing comprises producing entangled photons having characteristics favorable for transmission through atmosphere.

11. The method of claim 10 wherein the step of producing comprises producing entangled photons having characteristics favorable for transmission through local atmosphere.

12. The method of claim 1 wherein the step of directing comprises directing the entangled photons a distance of at least ten kilometers to the material.

13. The method of claim 1 wherein the step of producing occurs at a different location from the step of observing.

14. The method of claim 1 wherein the step of producing comprises producing entangled photons configured to minimize bleaching of the material.

15. The method of claim 1 further comprising producing entangled photons having a second known value of the at least one entangled photon parameter, and repeating the steps of directing, observing, and deducing.

16. The method of claim 15 wherein the entangled photons having the known value of the at least one entangled photon parameter and the entangled photons having the second known value of the at least one known entangled photon parameter have the same sum frequency.

17. A system for determining spectroscopic properties of a material, the system comprising:

a source of entangled photons configured to produce entangled photons having a known value of at least one entangled photon parameter;

optics configured to direct the entangled photons having the known value of at least one entangled photon parameter to a material over a distance of at least one kilometer;

optics configured to observe indicia of entangled photon absorption by the material; and a processor configured to compute at least one spectroscopic property of the material based on at least the indicia of entangled photon absorption and the known value of at least one entangled photon parameter.

18. The system of claim 17 wherein the entangled photon parameter is selected from the group consisting of: entanglement area, entanglement time, sum frequency, idler photon frequency, interbeam delay, and polarization.

19. The system of claim 17 wherein the at least one spectroscopic property of the material is selected from the group consisting of: at least one energy difference value, at least one transition matrix magnitude, at least one cross section, a spectral analysis function, and at least one energy level difference.

20. The system of claim 17 wherein the at least one spectroscopic property of the material comprises a function of at least one variable, the at least one variable selected from the group consisting of: entanglement area, entanglement time, energy, sum frequency, idler photon frequency, and interbeam delay.

21. The system of claim 17 wherein the material is selected from the group consisting of: a nerve agent, spores, bacteria, viruses, amino acids, a material with a radioactive isotope, and chlorine gas.

22. The system of claim 17 wherein the indicia of entangled photon absorption is selected from the group consisting of: fluorescence, phosphorescence, direct electron transfer, and ionization.

23. The method of claim 17 wherein the material is selected from the group consisting of: a gas, a solid, a liquid, an aerosol, and a colloid.

24. The system of claim 17 wherein the material is an organic chemical.

25. The system of claim 17 further comprising stored spectroscopic data and a processor configured to identify the material by comparing the deduced at least one spectroscopic property of the material with the stored spectroscopic data.

26. The system of claim 17 wherein the step of producing comprises producing entangled photons having characteristics favorable for transmission through atmosphere.

27. The system of claim 26 wherein the step of producing comprises producing entangled photons having characteristics favorable for transmission through local atmosphere.

28. The system of claim 17 wherein the optics configured to direct the entangled photons are configured to direct the entangled photons a distance of at least ten kilometers to the material.

29. The system of claim 17 wherein the optics configured to direct are at a different location from the optics configured to observe.

30. The system of claim 17 wherein the source of entangled photons is configured to produce entangled photons configured to minimize bleaching of the material.

31. The system of claim 17 wherein the source of entangled photons is configured to produce entangled photons having a second known value of the at least one entangled photon parameter.

32. The system of claim 31 wherein the entangled photons having a known value of at least one entangled photon parameter and the entangled photons having a second known value of at least one entangled photon parameter have the same sum frequency.

33. A system for determining spectroscopic properties of a material, the system comprising:
   means for producing entangled photons having a known value of at least one entangled photon parameter;
   means for directing the entangled photons having the known value of at least one entangled photon parameter to a material over a distance of at least one kilometer;
   means for observing indicia of entangled photon absorption by the material; and
   means for computing at least one spectroscopic property of the material based on at least the indicia of entangled photon absorption and the known value of at least one entangled photon parameter.

* * * * *